(12) United States Patent
Norcini et al.

(10) Patent No.: US 6,790,885 B2
(45) Date of Patent: Sep. 14, 2004

(54) THERMALLY STABILIZED POLYVINYL CHLORIDE COMPOSITIONS

(75) Inventors: Gabriele Pietro Norcini, Vizzola Ticino (IT); Guido Allieri, Goria Maggiore (IT); Angelo Roberto Casiraghi, Milan (IT); Mauro Ferracini, Ferno (IT); Marco Visconti, Varesa (IT); Giuseppe Li Bassi, Gavirate (IT)

(73) Assignee: Lamberti SpA, Albizzate (IT)

( * ) Notice: Subject to any disclaimer, the term of this patent is extended or adjusted under 35 U.S.C. 154(b) by 378 days.

(21) Appl. No.: 09/907,173

(22) Filed: Jul. 17, 2001

(65) Prior Publication Data
US 2003/0109607 A1 Jun. 12, 2003

(30) Foreign Application Priority Data
Aug. 19, 2000 (IT) ........................... VA00A0023

(51) Int. Cl.$^7$ ................................ C08K 5/34
(52) U.S. Cl. ........................ 524/100; 525/204
(58) Field of Search ............................ 524/100; 525/204

(56) References Cited

U.S. PATENT DOCUMENTS

| | | | |
|---|---|---|---|
| 3,532,699 A | 10/1970 | Kugele | 260/260 |
| 4,117,029 A * | 9/1978 | Kitano | 524/100 |
| 4,656,209 A | 4/1987 | Wehner et al. | 524/87 |
| 4,904,714 A * | 2/1990 | Raynor et al. | 524/100 |
| 5,925,696 A | 7/1999 | Wehner et al. | 524/100 |
| 6,084,013 A | 7/2000 | Wehner | 524/100 |
| 6,090,820 A | 7/2000 | Barbachyn et al. | 514/300 |
| 6,156,830 A * | 12/2000 | Wehner et al. | 524/100 |

FOREIGN PATENT DOCUMENTS

| | | |
|---|---|---|
| DE | DT1694873 | 8/1970 |
| EP | 0354179 B1 | 8/1994 |
| EP | 0967208 A1 | 12/1999 |
| EP | 0967209 A1 | 12/1999 |
| EP | 0967245 A1 | 12/1999 |
| GB | 2318188 A | 4/1998 |
| WO | WO00/68207 | 11/2000 |

* cited by examiner

*Primary Examiner*—Peter D. Mulcahy
(74) *Attorney, Agent, or Firm*—Madan, Mossman & Sriram, P.C.

(57) ABSTRACT

Disclosed are chlorine containing polymer compositions containing stabilizers which impart good thermal stability. PVC compositions and, in particular, flexible PVC compositions containing stabilizers which are oligomeric and/or polymeric aminouracyls exhibit high thermal stability as evidenced by improved resistance to yellowing and blistering upon extended exposure to high temperatures.

9 Claims, No Drawings

THERMALLY STABILIZED POLYVINYL CHLORIDE COMPOSITIONS

BACKGROUND OF THE INVENTION

1. Field of the Invention

The present invention relates to polyvinyl chloride compositions. The present invention particularly relates to flexible polyvinyl chloride compositions exhibiting high thermal stability.

2. Description of the Prior Art

Chlorine containing polymers in general and polyvinyl chloride (PVC) compositions in specific are well known materials having a wide variety of commercial uses. As are most polymers, chlorine containing polymers can be subject to thermal and oxidative decomposition. U.S. Pat. No. 6,096,820 to Lockledge, et al., describes using a synthetic crystalline aluminosilicate to impart thermal stability to PVC. Materials such as the aluminosilicates can impart properties to polymers which are not always desirable.

Other materials are known in the art to act as stabilizers. For example, the patents DE 1694873, U.S. Pat. Nos. 4,656,209, 5,925,696, GB (A) 2,318,188A, EP (A1) 967 209, EP (A1) 967 245, and EP (A1) 967208 describe using monomeric aminouracyls and aminothiouracyls as PVC stabilizers.

It would be desirable in the art of preparing chlorine containing polymers to prepare such polymers with stabilizers which allow for the preparation of a fully transparent stabilized system which can be processed at high temperatures for long periods without staining or blistering. It would also be desirable in the art to prepare such polymers where the polymer is PVC. It would be even more desirable in the art if the PVC were a flexible PVC.

SUMMARY OF THE INVENTION

In one aspect, the present invention is a chlorine-containing polymer composition exhibiting high thermal and oxidative stability comprising a chlorine-containing polymer and a stabilizer selected from the group consisting of oligomeric aminouracyls, polymeric aminouracyls and mixtures thereof.

In another aspect, the present invention is a stabilizer composition suitable for the stabilization of chlorine containing polymers comprising an oligomeric and/or polymeric aminouracyl compound having a structure of: (a) repeating units of general formula (I):

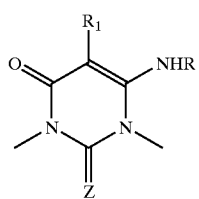

(I)

wherein:
R is selected from the group consisting of H; a $C_1$–$C_{18}$ linear or branched alkyl; a $C_5$–$C_8$ cycloalkyl; an aryl; an aryl substituted with —OH or $C_1$–$C_8$ alkoxy (here and hereafter called "substituted aryl"); an arylalkyl; an alkylaryl; and mixtures thereof;

$R_1$ is selected from the group consisting of H; a —(C=O)—$C_1$–$C_{12}$ linear or branched alkyl; a —(C=O)—O—$C_1$–$C_{12}$ linear or branched alkyl; a —(C=O) phenyl, wherein the phenyl is unsubstituted or substituted with —OH; a $C_1$–$C_8$ linear or branched alkyl; a $C_1$–$C_8$ alkoxy;
and mixtures thereof; and Z is O or S;

(b) linking groups between the repetitive groups of formula (I) which are the same or different and are selected from the group consisting of: —$(CR_2R_3)_n$—, wherein n is an integer having a value of from 2 to 12 and $R_2$ and $R_3$ can be the same or different and each independently of the other is selected from the group consisting of H, a $C_1$–$C_{12}$ linear, branched or cyclic alkyl, and mixtures thereof; 3-methylene-3,5,5-trimethylcyclohexan-1-yl; methylenebis(4-cyclohexyl); methylenebis(3-cyclohexyl); 1,4-phenylene; 1-methyl-2,4-phenylene; 4,4'-diphenylenemethane; and mixtures thereof;

(c) terminal groups selected from the group consisting of: H; a $C_1$–$C_{18}$ linear or branched alkyl; a $C_5$–$C_8$ cycloalkyl; a $C_3$–$C_{18}$ alkenyl; an aryl; a substituted aryl; an arylalkyl; an alkylaryl; a $C_1$–$C_{18}$ hydroxyalkyl; a $C_2$–$C_{18}$ alkoxy alkyl; a $C_6$–$C_{10}$ cycloalkoxyalkyl; a $C_7$–$C_{14}$ alkoxyaryl; a $C_7$–$C_{14}$ aryloxyalkyl; a $C_2$–$C_8$ alkylthioalkyl; a $C_6$–$C_{10}$ cycloalkylthioalkyl; a $C_7$–$C_{14}$ arylthioalkyl; a $C_7$–$C_{14}$ arylthioalkyl; a $C_1$–$C_{18}$ alkylamine, disubstituted with a $C_1$–$C_{18}$ linear or branched alkyl; and mixtures thereof.

DETAILED DESCRIPTION OF THE PREFERRED EMBODIMENTS

According to the present invention, flexible PVC compositions with high thermal stability can be prepared using oligomeric and/or polymeric aminouracyls as stabilizers. These stabilizers are compounds having a structure of: (a) repeating units of general formula (I):

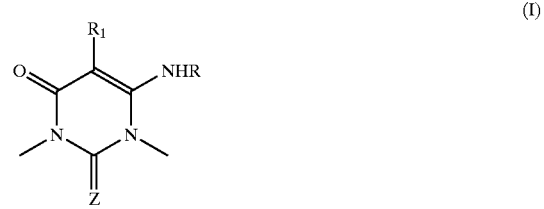

(I)

wherein:
R is selected from the group consisting of H; a $C_1$–$C_{18}$ linear or branched alkyl; a $C_5$–$C_8$ cycloalkyl; an aryl; a substituted aryl; an arylalkyl; an alkylaryl; and mixtures thereof, $R_1$ is selected from the group consisting of H; a —(C=O)—$C_1$–$C_{12}$ linear or branched alkyl;
a —(C=O)—O—$C_1$–$C_{12}$ linear or branched alkyl; a —(C=O) phenyl, wherein the phenyl is unsubstituted or substituted with —OH; a $C_1$–$C_8$ linear or branched alkyl; a $C_1$–$C_8$ alkoxy;
and mixtures thereof; and Z is O or S;

(b) linking groups between the repetitive groups of formula (I) which are the same or different and are selected from the group consisting of: —$(CR_2R_3)_n$—, wherein n is an integer having a value of from 2 to 12 and $R_2$ and $R_3$ can be the same or different and each independently of the other is selected from the group consisting of H, a $C_1$–$C_{12}$ linear, branched or cyclic alkyl; and mixtures thereof; 3-methylene-3,5,5-trimethylcyclohexan-1-yl; methylenebis(4-cyclohexyl); methylenebis(3-cyclohexyl); 1,4-phenylene; 1-methyl-2,4-phenylene; and 4,4'-diphenylenemethane;

(c) terminal groups selected from the group consisting of: H; a $C_1$–$C_{18}$ linear or branched alkyl; a $C_5$–$C_8$ cycloalkyl; a $C_3$–$C_{18}$ alkenyl; an aryl; a substituted aryl; an arylalkyl; an alkylaryl; a $C_1$–$C_{18}$ hydroxyalkyl; a $C_2$–$C_{18}$ alkoxy alkyl; a $C_6$–$C_{10}$ cycloalkoxyalkyl; a $C_7$–$C_{14}$ alkoxyaryl; a $C_7$–$C_{14}$ aryloxyalkyl; a $C_2$–$C_8$ alkylthioalkyl; a $C_6$–$C_{10}$ cycloalkylthioalkyl; a $C_7$–$C_{14}$ alkylthioaryl; a $C_7$–$C_{14}$ arylthioalkyl; a $C_1$–$C_{18}$ alkylamine, disubstituted with a $C_1$–$C_{18}$ linear or branched alkyl; and mixtures thereof.

Preferably, in general formula I, R is selected from the group consisting of: H, a $C_1$–$C_{18}$ linear or branched alkyl, a $C_5$–$C_8$ cycloalkyl, an aryl, an aryl substituted with —OH or $C_1$–$C_8$ alkoxy, and mixtures thereof; $R_1$ is H; and the terminal groups are selected from the group consisting of: H; a $C_1$–$C_{18}$ linear or branched alkyl; a $C_5$–$C_8$ cycloalkyl; a $C_3$–$C_{18}$ alkenyl; an aryl; an aryl substituted with —OH or $C_1$–$C_8$ alkoxy; a $C_1$–$C_{18}$ alkylamine, disubstituted with $C_1$–$C_{18}$ linear or branched alkyl; and mixtures thereof.

Oligomeric and/or polymeric aminouracyls according to the present invention have a mean molecular weight of from 280 and 5,000.

Oligomeric and/or polymeric aminouracyls according to the present invention are normally obtained by cyclization of an oligomeric and/or polymeric urea using cyanacetic acid or its derivatives. The product thus obtained can be further derivatized to give compounds where R and $R_1$ are different from H.

Preferably, the cyclization is carried out on a polyurea prepared by oligomerization and/or polymerization using suitable combinations of:

(A) a diisocyanate (DD) of formula OCN—Y—NCO wherein Y is selected from the group consisting of: —($CR_2R_3$)$_n$—, wherein n is an integer having a value of from 2 to 12 and $R_2$ and $R_3$ are the same or different and each independently of the other is selected from the group consisting of H, a $C_1$–$C_{12}$ linear or branched or cyclic, and mixtures thereof; 3-methylene-3,5,5-trimethylcyclohexan-1-yl; methylenebis(4-cyclohexyl); methylenebis(3-cyclohexyl); 1,4-phenylene; 1-methyl-2,4-phenylene; 4,4'-diphenylenemethane; and mixtures thereof;

(B) an amine (A) of the general formula X—NH$_2$ wherein X is selected from the group consisting of: H; a $C_1$–$C_{18}$ linear or branched alkyl; a $C_5$–$C_8$ cycloalkyl; $C_3$–$C$_alkenyl; an aryl; a substituted aryl; an arylalkyl; an alkylaryl; a $C_1$–$C_{18}$ hydroxyalkyl; a $C_2$–$C_{18}$ alkoxy alkyl; a $C_6$–$C_{10}$ cycloalkoxyalkyl; a $C_7$–$C_{14}$ alkoxyaryl; a $C_7$–$C_{14}$ aryloxyalkyl; a $C_2$–$C_8$ alkylthioalkyl; a $C_6$–$C_{10}$ cycloalkylthioalkyl; a $C_7$–$C_{14}$ alkylthioaryl; a $C_7$–$C_{14}$ arylthioalkyl; a $C_1$–$C_{18}$ alkylamine, disubstituted with $C_1$–$C_{18}$ linear or branched alkyl; and mixtures thereof;

(C) a diamine (AA) of the general formula H$_2$N—K—NH$_2$ wherein K is selected from the group consisting of:—($CR_2R_3$)$_n$—, wherein n is an integer having a value of 2 to 12 and $R_2$ and $R_3$ are the same or different and each independently of the other is selected from the group consisting of H, a $C_1$–$C_{12}$ linear or branched or cyclic alkyl, and mixtures thereof; 3-methylene-3,5,5-trimethylcyclohexan-1-yl; methylenebis(4-cyclohexyl); methylenebis(3-cyclohexyl); 1,4-phenylene; 1-methyl-2,4-phenylene; 4,4'-diphenylenemethane and mixture thereof; and (D) an isocyanate of formula W—NCO (D), where W is selected from the group consisting of: a $C_1$–$C_{18}$ linear or branched alkyl; a $C_5$–$C_8$ cycloalkyl; a $C_3$–$C_{18}$ alkenyl; an aryl; a substituted aryl; an arylalkyl; an alkylaryl; a $C_1$–$C_{18}$ hydroxyalkyl; a $C_2$–$C_{18}$ alkoxy alkyl; a $C_6$–$C_{10}$ cycloalkoxyalkyl; a $C_7$–$C_{14}$ alkoxyaryl; a $C_7$–$C_{14}$ aryloxyalkyl; a $C_2$–$C_8$ alkylthioalkyl; a $C_6$–$C_{10}$ cycloalkylthioalkyl; a $C_7$–$C_{14}$ alkylthioaryl; a $C_7$–$C_{14}$ arylthioalkyl; a $C_1$–$C_{18}$ alkylamine, disubstituted with $C_1$–$C_{18}$ linear or branched alkyl; and mixtures thereof.

According to the present invention in the preparation of the polyurea A, AA, D, DD can be used in all possible ratios. In the preferred embodiments, when AA and D are both equal to zero, the molar ratio DD/A is comprised between 0.3 and 0.6; when DD and A are both equal to zero, the molar ratio AA/D is comprised between 0.3 and 0.6. Obviously, the above description which was done assuming that Z is O in the repetitive group of formula (I) can be similarly repeated when Z is S by using the corresponding sulphurated compounds; in this case D and DD mean the corresponding isothiocyanate and diisothiocyanate.

According to the present invention, in flexible PVC compositions with a high thermal stability, the oligomeric and/or polymeric aminouracyl stabilizers may be incorporated in an amount of from 0.01 to 10% by weight, preferably of from 0.05 to 5% and most preferably of from 0.1 to 3% based on the entire composition.

According to the present invention, stabilized PVC compositions can further contain customary additives such as, but not exclusively: stabilizers, auxiliaries and processing aids, compounds containing alkali metal compounds and alkaline earth metal compounds, lubricants, plasticizers, pigments, fillers, phosphites, thiophosphites, thiophosphates, mercaptocarboxylates, epoxidized fatty acid esters, antioxidants, UV absorbers and light stabilizers, fluorescent whitening agents, impact modifiers, gelling agents and antistatic agents, metals deactivators, flame retardants, blowing agents and antifogging agents.

Examples of plasticizers that can be used according to the present invention are: esters of $C_4$–$C_{20}$ alcohols such as adipates, phthalates, trimellitates, azelates, sebacates, benzoates, phosphates; epoxidized compounds, typically epoxidized soy-bean oil; polymeric plasticizers such as polyester, polyadipates, polyphosphates, and the like.

The compounds of the present invention are useful as stabilizers for chlorine containing polymers such as polymers of vinyl chloride, vinyl resins containing vinyl chloride units in the structure, such as copolymers of vinyl chloride and vinyl esters of aliphatic acids, preferably vinyl acetate, copolymers of vinyl chloride with esters of acrylic and methacrylic acid and with acrylonitrile, copolymers of vinyl chloride with diene compounds and unsaturated dicarboxylic acids or their anhydrides, such as copolymers of vinyl chloride with diethyl maleate, diethyl fumarate or maleic acid anhydride, post-chlorinated polymers and copolymers of vinyl chloride and vinyliden chloride with unsaturated aldehydes and ketones, such as acrolein, crotonaldehyde, vinyl methyl ketone, vinylmethylether, vinyl isobutylether and the like; polymers of vinylidene chloride and copolymers thereof with vinyl chlorides or other polymerizable compounds; polymers of vinyl chloroacetate and dichlorovinyl ether; chlorinated polymers of vinyl acetate, chlorinated polymeric esters of acrylic acid and of α-substituted acrylic acid; polymers of chlorinated styrene; chlorinated rubbers; chlorinated polymers of ethylene; polymers and post-chlorinated polymers of chlorobutadiene and their copolymers with vinyl chloride, chlorinated rubber; mixtures of the cited polymers alone or with other polymerizable compounds. Included in these materials are also graft polymers of PVC with EVA, ABS and MBS. Preferred substrates are also mixtures of above homo and copolymers, preferably homopolymers of vinyl chloride with other thermoplastic or elastomeric polymers, in particular blends with ABS, MBS, NBR, SAN, EVA, CPE, MBAS, PMA, PMMA, EPDM and polylactones.

Suitable compositions for use with the stabilizers of the present invention are preferably recycled chlorine containing polymers. These polymers are the above mentioned polymers which have suffered damage through use, storage or production process. Particularly preferred is recycled PVC. Recycled products may also contain minor amounts of foreign material difficult to remove, such as paper, pigments, adhesives.

The compositions of PVC containing the stabilizers of the present invention, show as their fundamental characteristic a high thermal stability together with a good transparency of the stabilized system, without staining and blistering. These properties of the compositions of PVC according to the invention, are very different from those described in the known art. This is demonstrated by the applicative results obtained on compositions of PVC containing the oligomeric and/or polymeric aminouracyls of the present invention.

EXAMPLES

The following examples are provided to illustrate the present invention. The examples are not intended to limit the scope of the present invention and they should not be so interpreted. Amounts are in weight parts or weight percentages unless otherwise indicated.

Example 1
Preparation of a Diuracyl

A solution of 19.2 g (150 millimoles (mmol)) of di n-octylamine in 22 ml of THF are added dropwise into 10 g (60 mmol) of 1,6-hexamethylene diisocyanate dissolved in 100 ml of THF under stirring at a temperature not exceeding 15° C. After the addition the reaction mixture is stirred for 30 min and allowed to reach room temperature. The reaction mixture is then poured into 400 ml of acetone. The obtained precipitate is filtered, washed with acetone and dried under vacuum. 25.2 g of a white solid are obtained.

IR: ($cm^{-1}$): 3333, 2955, 2929, 2853, 1616, 1577).

5 g (11.7 mmol) of the solid are reacted under stirring with 2.87 g (28.1 mmol) of acetic anhydride and 2.2 g (25.9 mmol) of cyanacetic acid. The mixture is heated at 90° C. and then the temperature is maintained for 2 hours at 80–90° C.

10 ml of water and a 15% sodium hydroxide are added to the reaction mixture solution to obtain pH>9, then the reaction mixture is refluxed for 1 hour. The reaction mixture is then cooled down to room temperature and it is diluted with methylene chloride.

After phase separation the organic layer is washed with water to neutral pH. The organic layer is dried on anhydrous sodium sulphate, then the solvent is evaporated under vacuum. 4.87 g of a brown solid are obtained.

IR: ($cm^{-1}$): 3349, 3207, 2926, 2855, 1623.
MS: 561 (M+1)
$^{13}$CNMR: (DMSO $d_6$): δ(ppm): 13.5, 21.6, 25.4, 26.0, 27.2, 28.5, 31.0, 41.4, 75.0, 151.0, 154.0, 161.0.

$^1$HNMR.(CDCl$_3$): δ(ppm): 0.85 (t, 6H); 1.25 (m, 24H); 1.61 (m, 8H); 3.88 (m, 8H); 5.02 (bs, 2H).

Example 2
Preparation of a Polyuracyl

A solution of 2.3 g (19.8 mmol) of 1,6-hexamethylenediamine in 30 ml of THF are added dropwise to 5 g (29.8 mmol) of 1,6-hexamethylene diisocyanate dissolved in 50 ml of THF under stirring at 5° C. After the addition the reaction mixture is allowed to reach room temperature and a solution of 2.9 g (22.5 mmol) of n-octylamine in 30 ml of THF are added dropwise. After stirring for 30 min at room temperature, the reaction mixture is poured into acetone, then it is dried under vacuum. 9.5 g of solid are obtained. (IR: ($cm^{-1}$): 3329, 2929, 2854, 1616, 1579.

4 g of the solid are reacted under stirring with 10 g (98 mmol) of acetic anhydride and 5 g (58.8 mmol) of cyanacetic acid. The mixture is heated at 90° C. under stirring for 4.5 hours. 10 ml of water and a 20% sodium hydroxide solution are added to the reaction mixture to obtain pH>9 then the reaction mixture is refluxed for 1.5 hours. The reaction mixture is cooled down to room temperature and a solid compound is obtained by decantation. The solid is dissolved in methylene chloride/methanol (1/1) and the insoluble residue is discarded. The organic layer is evaporated under vacuum. 5.14 g of a brown solid are obtained.

IR ($cm^{-1}$): 3419, 3252, 2927, 2855, 1628, 1575.
$^{13}$CNMR: (DMSO $d_6$): δ(ppm): 13.5, 21.5, 25.5, 26.0, 27.0, 27.2, 28.5, 29.6, 31.0, 41.5, 75.0, 151.0, 154.0, 161.0.
$^1$HNMR: (DMSO $d_6$): δ(ppm): 0.82 (m, 6H); 1.20 (m, 37H); 1.44 (m, 17H); 3.50–3.90 (m, 23H); 4.66 (bs, 3.75H).

Example 3
Preparation of a Lipophylic Diuracyl

A solution of 1.96 g (16.9 mmol) of 1,6-hexamethylenediamine in 50 ml of THF are added dropwise to 10 g (33.84 mmol) of octadecyl isocyanate dissolved in 100 ml of THF under stirring and at a temperature not exceeding 10° C. After the addition the reaction mixture is allowed to reach room temperature and then stirred for 30 min. The precipitate thus obtained is filtered. 10.97 g of a white solid are obtained.

IR: ($cm^{-1}$): 3336, 2920, 2849, 1615, 1575).

5 g (7.08 mmol) of the solid are reacted under stirring with 1.73 g (17 mmol) of acetic anhydride and 1.32 g (15.58 mmol) of cyanacetic acid. The mixture is stirred and heated at 95° C. for 3 hours. 10 ml of water and a 20% sodium hydroxide solution are added to the reaction mixture to obtain pH>9 then the reaction mixture is refluxed for 1 hour. The reaction mixture is cooled down to room temperature, the insoluble residue is filtered off and the remaining part is redissolved with ethyl acetate. The organic layer is washed with water and is dried on anhydrous sodium sulphate, then the solvent is evaporated under vacuum. 4.45 g of a brown solid are obtained.

IR ($cm^{-1}$): 3353, 3206, 2921, 2851, 1623.
$^{13}$CNMR: (DMSO $d_6$): δ(ppm): 13.4, 21.8, 25.7, 27.2, 28.7, 31.0, 41.3, 75.0, 151.0, 153.9, 161.0.
$^1$HNMR: δ(ppm): 0.87 (m, 6H); 1.25 (m, 64H); 1.63 (m, 8H); 3.76 (m, 8H); 5.00 (bs, 2H).

Example 4
Preparation of a Polyacyl

A solution of 2.42 g (20.86 mmol) of 1,6-hexamethylenediamine in 30 ml of THF are added dropwise to 7 g (41.67 mmol) of hexamethylene diisocyanate dissolved in 100 ml of THF under stirring and at 5° C. After the addition the reaction mixture is allowed to reach spontaneously 15° C., then a solution of 6.38 g (49.46 mmol) of n-octylamine in 40 ml of THF are added dropwise. The reaction mixture is stirred for 30 min at room temperature then it is filtered and the obtained precipitate is washed with acetone. 13.72 g of crude product are obtained. (IR: (cm$^{-1}$): 3337, 2928, 2854, 1620, 1576).

5 g of the solid are reacted under stirring with 3.23 g (31.69 mmol) of acetic anhydride and 2.51 g (29.58 mmol) of cyanacetic acid. The mixture is heated at 100° C. under stirring for 3.5 hours. 10 ml of water and a 15% sodium hydroxide solution are added to the reaction mixture to obtain pH 9 then the reaction mixture is refluxed for 2.5 hours. The reaction mixture is cooled down to room temperature and a solid compound is obtained by decantation. The solid is dissolved in methylene chloride/methanol (1/1) and the insoluble residue is discarded. The organic layer is evaporated under vacuum. 6.74 g of a yellow solid are obtained.

IR (cm$^{-1}$): 3414, 2927, 2854, 1631, 1574.
$^{13}$CNMR: (DMSO d$_6$): δ(ppm): 13.4, 21.8, 25.8, 27.3, 28.4, 29.8, 31.0, 41.5, 75.0, 151.0, 154.1, 161.2.
$^1$HNMR: δ(ppm): 0.86 (m, 6H); 1.27 (m, 32H); 1.47 (m, 16H); 3.25 (m, 16H); 467 (bs, 4H).

Example 5
Preparation of a Diuracyl With Unsaturated Side Chains

According to the procedure described in Example 1, starting from 2 g (11.9 mmol) of hexamethylene diisocyanate in 50 ml of THF and 7.64 g (28.57 mmol) of oleylamine in 30 ml of THF, 8.38 g of a white solid are obtained.

5 g (7.12 mmol) of the solid are reacted with 1.33 g (15.6 mmol) of cyanacetic acid and 1.67 g (16.4 mmol) of acetic anhydride; the reaction mixture is treated as reported in Example 1 to obtain 4.06 g of a light yellow solid.

IR (cm$^{-1}$): 3386, 3214, 2924, 2853, 1620, 966.
$^{13}$CNMR: (DMSO d6): δ(ppm): 13.8, 21.9, 25.5, 26.6, 27.6, 28.5, 29.0, 31.1, 41.6, 75.0, 129.2, 151.0, 154.0, 161.0.
$^1$HNMR: (DMSO d6): δ(ppm): 0.84 (t, 6H); 1.24 (m, 48H); 1.50 (m, 8H); 1.96 (m, 8H); 3.63–3.83 (m, 8H); 4.65 (s, 2H); 5.32 (m, 4H).

Example 6
Preparation of a Diuracyl

According to the procedure described in Example 1, starting from 10 g (45 mmol) of 3-methylene-3,5,5-trimethylcyclohexan-1-yl diisocyanate into 200 ml of THF and 12.77 g (99 mmol) of octylamine into 100 ml of THF, 16.35 g of a white solid are obtained.

5 g (10.42 mmol) of the solid are reacted with 1.96 g (23.06 mmol) of cyanacetic acid and 2.45 g (24.10 mmol) of acetic anhydride; the reaction mixture is treated as reported in Example 1 to obtain 5.51 g of a light yellow solid.

IR (cm$^{-1}$): 3359, 3261, 3213, 2955, 2926, 2855, 1623.
$^{13}$CNMR: (DMSO d6): δ(ppm): 13.5, 21.7, 26.0, 27.2, 28.4, 29.7, 30.9, 35.0, 42.1, 46.4, 52.3, 75.2, 151.9, 154.6, 155.0, 160.9.
$^1$HNMR: (DMSO d6): δ(ppm): 0.75–1.70 (m, 45H); 3.50–3.90 (m, 7H); 4.60–4.85 (m, 2H).

Example 7
Preparation of a Diuracyl

According to the procedure described in Example 1, starting from 10 g (38.12 mmol) of methylene-bis(4-cyclohexylisocyanate), alias 4,4A'-methylene-bis (cyclohexyl isocyanate, into 200 ml of THF and 10.82 g (83.86 mmol) of octylamine into 100 ml of THF, 16.30 g of a white solid are obtained.

5 g (19.62 mmol) of the solid are reacted with 1.80 g (21.15 mmol) of cyanacetic acid and 2.26 g (22.11 mmol) of acetic anhydride; the reaction mixture is treated as reported in Example 1 to obtain 5.97 g of a yellow solid.

IR (cm$^{-1}$): 3384, 3212, 2925, 2853, 1631, 1560.
$^{13}$CNMR: (DMSO d6): δ(ppm): 13.5, 21.7, 26.1, 28.3, 29.7, 30.9, 33.1, 44.5, 48.3, 55.2, 76.2, 150.7, 154.6, 157.3, 161.1.
$^1$HNMR: (DMSO d6): δ(ppm): 0.70–1.95 (m, 50H); 3.50–3.82 (m, 4H); 3.85–4.15 (m, 2H); 4.60–4.75 (m, 2H).

The relevant data of Examples from 1 to 7 are summarized in Table 1.

TABLE I

| | Substituents | | | Reagents | | | | | |
| --- | --- | --- | --- | --- | --- | --- | --- | --- | --- |
| | formula (I) | | | X—NH$_2$ | W—NCO | OCN—Y—NCO | H$_2$N—K—NH$_2$ | Molar ratios | | |
| Examples | R | R$_1$ | Z | X | W | Y | K | DD/AA | DD/A | AA/D |
| 1 | H | H | O | CH$_3$(CH$_2$)$_7$ | — | (CH$_2$)$_6$ | — | — | 0.40 | — |
| 2 | H | H | O | CH$_3$(CH$_2$)$_7$ | — | (CH$_2$)$_6$ | (CH$_2$)$_6$ | 1.50 | 1.32 | — |
| 3 | H | H | O | — | CH$_3$(CH$_2$)$_{17}$ | — | (CH$_2$)$_6$ | — | — | 0.50 |
| 4 | H | H | O | CH$_3$(CH$_2$)$_7$ | — | (CH$_2$)$_6$ | (CH$_2$)$_6$ | 2.00 | 0.84 | — |
| 5 | H | H | O | CH$_3$(CH$_2$)$_7$CH=CH(CH$_2$)$_8$ | — | (CH$_2$)$_6$ | — | — | 0.42 | — |
| 6 | H | H | O | CH$_3$(CH$_2$)$_7$ | — | (trimethylcyclohexyl-CH$_2$—) | — | — | 0.46 | — |

TABLE I-continued

| | Substituents | | | | Reagents | | | | | |
|---|---|---|---|---|---|---|---|---|---|---|
| | formula (I) | | | X—NH$_2$ | W—NCO | OCN—Y—NCO | H$_2$N—K—NH$_2$ | | Molar ratios | |
| Examples | R | R$_1$ | Z | X | W | Y | K | DD/AA | DD/A | AA/D |
| 7 | H | H | O | CH$_3$(CH$_2$)$_7$ | — | (cyclohexyl-CH$_2$-cyclohexyl) | — | — | 0.45 | — |

Example 8
Preparation of a Dithiouracyl

A solution of 11 g (80 mmol) of thiophenyl isocyanate in 50 ml of THF are added dropwise to 4.22 g (36 mmol) of hexamethylene diamine dissolved in 100 ml of THF under stirring and at a temperature not exceeding 10° C. After the addition the reaction mixture is allowed to reach room temperature and then stirred for 2 hours. Then the solvent is evaporated under vacuum and 14 g of a white solid are obtained.

IR: (cm$^{-1}$): 3172, 3010, 2926,1594, 1534, 1452.
$^1$HNMR (DMSO d$_6$): δ(ppm): 1.25–1.45 (m, 4H); 1.50–1.70 (m, 4H); 3.45–3.55 (m, 4H); 7.07 (m, 2H); 7.3 (m, 4H); 7.45 (m, 4H); 7.6 (m, 2H).
MS: 387 (M+1)

1.5 g (3.88 mmol) of the white solid are reacted under stirring with 0.84 g (8.23 mmol) of acetic anhydride and 0.7 g (8.23 mmol) of cyanacetic acid. The mixture is stirred and heated at 60° C. for 3 hours. 10 ml of water and a 5% sodium hydroxide solution are added to the reaction mixture to obtain pH 9–10, then the reaction mixture is refluxed for 2 hours. The reaction mixture is cooled down to room temperature and methylene chloride is added. The organic layer is separated, washed with water, dried on anhydrous sodium sulphate and then the solvent is evaporated under vacuum. 1.13 g of a solid are obtained.

The solid is purified by chromatography (silica gel, eluent: petroleum ether-ethylacetate 70:30 to 60:40). 0.12 g of purified dithiouracyl is obtained.

$^1$HNMR (DMSO d$_6$) δ(ppm): 1.25–1.50 (m, 4H); 1.50–1.80 (m, 4H); 3.45–3.65 (m, 4 H); 5.70 (3, 2H); 7.25–7.50 (m, 10H).
MS: 521 (M+1)

Example 9
Preparation of a Diuracyl with Diphenylaliphatic Internal Chain and Aliphatic Side Chain A solution of 11.36 g (87.9 mmol) of n-octylamine in 100 ml of THF are added dropwise to 10 g (40 mmol) of methylene bis(4-phenylisocyanate) dissolved in 200 ml of THF under stirring and at a temperature not exceeding 10° C. After the addition the reaction mixture is allowed to reach room temperature and then stirred for 30 min. The precipitate is then filtered, washed with acetone and dried under vacuum. 20 g of a white solid are obtained.

IR: (cm$^{-1}$): 3441, 3326, 2955, 2925, 2852, 1632, 1599, 1561. 5 g (98 mmol) of the white solid are reacted under stirring with 2.4 g (23.6mmol) of acetic anhydride and 1.84 g (21.6 mmol) of cyanacetic acid. The mixture is stirred and heated at 105° C. and the temperature is set at 90–100° for 3 hours. 20 ml of water and a 15% sodium hydroxide solution are added to the reaction mixture to obtain pH>9, then the reaction mixture is refluxed for 2 hour. The reaction mixture is cooled down to room temperature and a solid compound is obtained by decantation. The solid is dissolved in methylene chloride. The organic layer obtained is washed with water and with a saturated solution of NaCl, then dried with sodium sulphate and evaporated under vacuum to obtain 6.1 g of a light yellow solid.

IR (cm$^{-1}$): 3473, 3319, 3247, 3191, 2954, 2925, 2854, 1635, 1547, 1510, 1473.
$^1$HNMR (DMSO d$_6$) δ(ppm): 0.75–0.95 (m, 6H); 1.1–1.35 (m, 20H); 1.35–1.60 (m, 4H); 3.60–4.05 (m, 4H); 4.83 (bs, 2H); 6.0 (m, 2H); 6.90–7.57 (m, 8H)
$^{13}$CNMR: (DMSO d6): δ(ppm): 13.4, 21.8, 26.0, 27.0, 28.5, 31.0, 74.8, 128.5, 129.5, 132.3, 141.2, 150.9, 154.0, 161.2.

Example 10
Preparation of a Diuracyl With Cycloaliphatic Side Chain

A solution of 14.5 g (146 mmol) of cyclohexylamine in 50 ml of THF are added dropwise to 12 g (71.4 mmol) of 1,6-hexamethylene diisocyanate dissolved in 150 ml of THF under stirring and at a temperature not exceeding 15° C. After the addition the reaction mixture is allowed to reach room temperature and then stirred for 30 min. then the precipitate is filtered, washed with THF and dried under vacuum. 24.5 g of a white solid are obtained.

IR: (cm$^{-1}$): 3346, 3314, 2929, 2854, 1624, 1574.

10 g (27 mmol) of the white solid are reacted under stirring with 6.1 g (60 mmol) of acetic anhydride and 5.1 g (60 mmol) of cyanacetic acid. The mixture is stirred and heated at 105° C. and the temperature is set at 90–100° for 3 hours. 20 ml of water and a 15% sodium hydroxide solution are added to the reaction mixture to obtain pH>9, then the reaction mixture is refluxed for 2 hours. The reaction mixture is cooled down to room temperature and a solid compound is obtained by decantation. The solid is dissolved in methylene chloride-methanol (1:1) and the insoluble residue is discarded. The organic layer is evaporated under vacuum to obtain 13.2 g of a brown solid. 5 g of the brown solid are purified by chromatography (silica gel, eluent: methylene chloride-methanol 95:5 to 80:20). 1 g of a purified diuracyl is obtained.

IR (cm$^{-1}$): 3362, 3210, 2930, 2855, 1620, 1478.

$^1$HNMR (DMSO d$_6$) δ(ppm): 0.95–1.95 (m, 24H); 2.2–2.4 (m, 4H); 3.6–3.8 (m, 4H) 3.85–4.15 (m, 2H); 4.7 ((bs, 2H).

MS: 501 (M+1).

Example 11
Preparation of a Diuracyl With Hydroxyaromatic Side Chain

A solution of 7.71 g (45.9 mmol) of 1,6-hexamethylene diisocyanate in 100 ml of THF are added dropwise to 10 g (91.7 mmol) of 3-amino-phenol dissolved in 150 ml of THF under stirring and at a temperature not exceeding 15° C. After the addition the reaction mixture is allowed to reach room temperature and then stirred for 1 hour. Then the precipitate is filtered, washed with slightly acidic water and dried under vacuum. 12.3 g of a white solid are obtained.

IR: (cm$^{-1}$): 3322, 2930, 2857, 1630, 1605, 1566, 1442.

2 g (5.2 mmol) of the white solid are reacted under stirring with 2.22 g (21.8 mmol) of acetic anhydride and 1.85 g (21.8 mmol) of cyanacetic acid. The mixture is stirred and heated at 90° C. and the temperature is set at 90–95° for 3 hours. 20 ml of water and a 15% sodium hydroxide solution are added to the reaction mixture to obtain pH>9, then the reaction mixture is refluxed for 2.5 hour. The reaction mixture is cooled down to room temperature and a solid compound is obtained by decantation. The solid is dissolved in methanol under reflux. The obtained solution is cooled, filtered and evaporated under vacuum to obtain 2.08 g of a crude solid. 2 g of the crude solid are purified by chromatography (silica gel, eluent: methylene chloride-methanol 95:5 to 90:10). 0.34 g of a purified diuracyl is obtained.

$^1$HNMR (DMSO d$_6$) δ(ppm): 1.25 (m, 4H); 1.50 (m, 4H); 3.67 (t, 4H); 4.77 (s, 2H); 6.65 (m, 2H); 6.70 (m, 2H); 6.87 (m, 2H); 7.30 (m, 2H).

MS: 521 (M+1).

The relevant data of Examples from 8 to 11 are summarized in Table I (a).

TABLE I(a)

| Examples | Substituents formula (I) | | | | Reagents | | | | Molar ratios | | |
|---|---|---|---|---|---|---|---|---|---|---|---|
| | R | R$_1$ | Z | X—NH$_2$ X | W—NCO W | W—NCS J | OCN—NCO Y | H$_2$N—K—NH$_2$ K | DD/AA | DD/A | AA/D |
| 8 | H | H | S | — | — | phenyl | — | (CH$_2$)$_6$ | — | — | 0.45 |
| 9 | H | H | O | CH$_3$(CH$_2$)$_7$ | — | — | diphenylmethane | — | — | 0.46 | — |
| 10 | H | H | O | cyclohexyl | — | — | (CH$_2$)$_6$ | — | — | 0.49 | — |
| 11 | H | H | O | 3-hydroxyphenyl | — | — | (CH$_2$)$_6$ | — | — | 2.00 | — |

APPLICATION TESTS—STATIC HEAT TESTS.

The thermal stability of PVC compositions stabilized with the products of the invention is measured as reported below.

A dry mixture of the ingredients reported in the following table, is laminated using a two cylinder apparatus for 1 min at 190° C. From the obtained rolled sheet, 20×220 mm samples are prepared. The test sample is subject to thermal stress in a Wherner Mathis oven equipped with a thermotester device. The oven temperature is set at 190° C. and the thermotester device is set so that 20 mm of test sample are removed from the oven at regular intervals. In the reported conditions the sample is under a static heat stress. At the end of the experiment the evaluation is carried out measuring the Yellow Index according to ASTM D-1925–70.

The results on rigid PVC (Compositions 1 and 2-Tab. II) and on flexible PVC (Compositions 3 and 4-Tab. III) are reported below. Low values of Yellow Index signify a good stabilisation.

Compositions 1 and 2 (numbers refer to parts by weight):

|  | Composition 1 | Composition 2 |
|---|---|---|
| S-PVC (k value 64) | 100 | 100 |
| Epoxidized soy-bean oil* | 2 | 2 |
| Compound of Example 1 | — | 0.4 |

*oxyranic oxygen > 6 g ($O_2$)/100 g

TABLE II

Static heat test

| Thermal stress duration (min.) | Y.I. Composition 1 | Y.I. Composition 2 |
|---|---|---|
| 3' | 11.5 | 5.1 |
| 6' | 29.3 | 5.9 |
| 9' | 41.3 | 13 |
| 12' | >100 (burning) | 22.4 |
| 15' |  | 38.5 |
| 18' |  | 55.6 |
| 21' |  | 73.3 |
| 24' |  | >100 (burning) |

Compositions 3 and 4 (numbers refer to parts by weight):

|  | Composition 3 | Composition 4 |
|---|---|---|
| S-PVC (k value 70) | 100 | 100 |
| Dioctyl phtalate | 60 | 60 |
| Stearic acid | 0.2 | 0.2 |
| Epoxidized soy-bean oil* | 2 | 2 |
| Compound of Example 1 | — | 0.4 |

*oxyranic oxygen > 6 g ($O_2$)/100 g

TABLE III

Static heat test

| Thermal stress duration (min.) | Y.I. Composition 3 | Y.I. Composition 4 |
|---|---|---|
| 4' | 5.5 | 3 |
| 8' | 8.3 | 4.9 |
| 12' | 25.8 | 10.9 |
| 16' | 44.7 | 20.7 |
| 20' | 62.5 | 33.5 |
| 24' | 70.7 | 45.5 |
| 28' | 74.1 | 59.7 |
| 32' | >100 (burning) | 70.8 |
| 36 |  | 77.3 |
| 40' |  | >100 (burning) |

In Table II(a) and in Tables from III(a) to III(e) the thermal stability of some other PVC compositions (Compositions 6–22) is reported.

Compositions 6 and 7 (numbers refer to parts by weight):

|  | Composition 6 | Composition 7 |
|---|---|---|
| S-PVC (k value 64) | 100 | 100 |
| Epoxidized soy-bean oil* | 2 | 2 |
| Compound of Example 4 | 0.4 | 0 |
| Compound of Example 6 | 0 | 0.4 |

*oxyranic oxygen > 6 g ($O_2$)/100 g

Compositions 8 and 9 (numbers refer to parts by weight):

|  | Composition 8 | Composition 9 |
|---|---|---|
| S-PVC (k value 70) | 100 | 100 |
| Dioctyl phtalate | 60 | 60 |
| Stearic Acid | 0.5 | 0.5 |
| Epoxidized soy-bean oil* | 2 | 2 |
| Compound of Example 4 | 0.4 | 0 |
| Compound of Example 6 | 0 | 0.4 |

*oxyranic oxygen > 6 g ($O_2$)/100 g

Compositions 10, 11, 12, 13 (numbers refer to parts by weight):

|  | Composition 10 | Composition 11 | Composition 12 | Composition 13 |
|---|---|---|---|---|
| S-PVC (k value 70) | 100 | 100 | 100 | 100 |
| Dioctyl phtalate | 40 | 40 | 40 | 40 |
| Ca/Zn liquid stabilizer** | 2 | 2 | 2 | 2 |
| Epoxidized soy-bean oil* | 2 | 2 | 0 | 0 |
| Compound of Example 4 | 0 | 0.2 | 0 | 0.2 |

*oxyranic oxygen > 6 g ($O_2$)/100 g
**Lastab CA 364 from Lagor SpA

Compositions 14, 15, 16 (numbers refer to parts by weight):

|  | Composition 14 | Composition 15 | Composition 16 |
|---|---|---|---|
| S-PVC (k value 70) | 100 | 100 | 100 |
| Dioctyl phtalate | 60 | 60 | 60 |
| Stearic Acid | 0.5 | 0.5 | 0.5 |
| Epoxidized soy-bean oil* | 2 | 2 | 2 |
| Compound of Example 1 | 0.1 | 0.3 | 1 |

*oxyranic oxygen > 6 g ($O_2$)/100 g

Compositions 17, 18, 19 (numbers refer to parts by weight):

|  | Composition 17 | Composition 18 | Composition 19 |
|---|---|---|---|
| S-PVC (k value 70) | 100 | 100 | 100 |
| Dioctyl phtalate | 60 | 60 | 60 |
| Stearic Acid | 0.5 | 0.5 | 0.5 |
| Epoxidized soy-bean oil* | 2 | 2 | 2 |
| Compound of Example 4 | 0.1 | 0.3 | 1 |

*oxyranic oxygen > 6 g ($O_2$)/100 g

Compositions 20, 21, 22 (numbers refer to parts by weight):

|  | Composition 20 | Composition 21 | Composition 22 |
|---|---|---|---|
| S-PVC (k value 70) | 100 | 100 | 100 |
| Dioctyl phtalate | 60 | 60 | 60 |
| Stearic Acid | 0.5 | 0.5 | 0.5 |
| Epoxidized soy-bean oil* | 2 | 2 | 2 |
| Compound of Example 6 | 0.1 | 0.3 | 1 |

*oxyranic oxygen > 6 g ($O_2$)/100 g

TABLE II

(a)-Static heat test

| Thermal stress duration (min.) | Y.I. Composition 6 | Y.I. Composition 7 |
|---|---|---|
| 4 | 9.85 | 7.56 |
| 8 | 15.25 | 10.64 |
| 12 | 33.39 | 20.11 |
| 16 | 52.91 | 33.61 |
| 20 | 67.73 | 52.23 |
| 24 | 79.15 | 67.84 |
| 28 | >100 (burning) | 77.47 |
| 32 |  | >100 (burning) |

TABLE III

(a)-Static heat test

| Thermal stress duration (min) | Y.I. Composition 8 | Y.I. Composition 9 |
|---|---|---|
| 4' | 7.14 | 6.04 |
| 8' | 11.47 | 12.45 |
| 12' | 18.83 | 19.37 |
| 16' | 27.55 | 30.59 |
| 20' | 38.04 | 40.01 |
| 24' | 52.30 | 50.71 |
| 28' | 67.12 | 60.53 |
| 32' | 74.29 | 70.00 |
| 36 | 75.59 | 76.58 |
| 40' | 78.55 | 77.31 |
| 44' | 81.85 | 79.58 |
| 48' | >100 (burning) | 84.56 |
| 52' |  | >100 (burning) |

TABLE III

(b)-Static heat test

| Thermal stress duration (min) | Y.I. Composition 10 | Y.I. Composition 11 | Y.I. Composition 12 | Y.I. Composition 13 |
|---|---|---|---|---|
| 4' | 0.85 | 5.07 | 1.23 | 4.32 |
| 8' | 0.90 | 4.53 | 1.25 | 6.00 |
| 12' | 2.17 | 7.24 | 2.46 | 8.99 |
| 16' | 3.92 | 11.44 | 3.28 | 10.86 |
| 20' | 6.96 | 13.62 | 3.61 | 12.78 |
| 24' | 18.18 | 17.90 | 29.94 | 13.94 |
| 28' | 36.77 | 39.16 | >100 (burning) | 14.58 |
| 32' | >100 (burning) | 59.68 |  | 17.37 |
| 36 |  | 75.81 |  | 27.34 |
| 40' |  | 83.79 |  | 70.59 |
| 44' |  | >100 (burning) |  | >100 (burning) |

TABLE III

(c)-Static heat test

| Thermal stress duration (min.) | Y.I. Composition 14 | Y.I. Composition 15 | Y.I. Composition 16 |
|---|---|---|---|
| 3' | 4.41 | 4.39 | 7.39 |
| 6' | 12.31 | 5.70 | 10.67 |
| 9' | 30.84 | 12.79 | 18.22 |
| 12' | 45.36 | 24.22 | 24.65 |
| 15' | 75.59 | 40.23 | 31.61 |
| 18' | >100 (burning) | 61.69 | 40.97 |
| 21' |  | 74.18 | 50.15 |
| 24' |  | 78.33 | 58.80 |
| 27' |  | >100 (burning) | 69.03 |
| 30' |  |  | 74.67 |
| 33' |  |  | >100 (burning) |

TABLE III

(d)-Static heat test

| Thermal stress duration (min.) | Y.I. Composition 17 | Y.I. Composition 18 | Y.I. Composition 19 |
|---|---|---|---|
| 3' | 5.85 | 3.50 | 11.73 |
| 6' | 18.78 | 6.53 | 11.55 |
| 9' | 38.96 | 15.98 | 17.22 |
| 12' | 63.53 | 28.64 | 25.62 |
| 15' | 69.84 | 53.01 | 34.92 |
| 18' | >100 (burning) | 71.06 | 48.58 |
| 21' |  | 76.41 | 61.37 |
| 24' |  | >100 (burning) | 70.89 |
| 27' |  |  | 77.10 |
| 30' |  |  | >100 (burning) |

TABLE III

(e)-Static heat test

| Thermal stress duration (min.) | Y.I. Composition 20 | Y.I. Composition 21 | Y.I. Composition 22 |
|---|---|---|---|
| 3' | 3.39 | 3.58 | 3.73 |
| 6' | 13.28 | 7.54 | 9.50 |
| 9' | 29.32 | 19.82 | 17.03 |
| 12' | 58.24 | 32.04 | 24.70 |
| 15' | 74.91 | 52.44 | 34.79 |
| 18' | >100 (burning) | 66.97 | 46.37 |
| 21' |  | 78.94 | 55.40 |
| 24' |  | 72.82 | 65.34 |
| 27' |  | >100 (burning) | 73.99 |
| 30' |  |  | 78.73 |
| 33' |  |  | >100 (burning) |

APPLICATION TESTS—EVALUATION OF STAINING AND BLISTERING.

The evaluation of staining and blistering stability is carried out by the evaluation, respectively, of exudation and transparency on test samples obtained from lamination using a two cylinder apparatus for 1 min at 190° C. The exudation is evaluated by an organoleptic test. An exudated sample is tacky. An empirical evaluation has been set up with scores from 0 to 3, according to the definitions of Table IV.

TABLE IV

| Degree of exudation | tacky of the test sample |
|---|---|
| 0 | Tack free |
| 1 | Lightly tacky |
| 2 | Moderately tacky |
| 3 | Strongly tacky |

Transparency is measured by a BYK Colour Guide 45/0 calorimeter using the setting to measure opacity. The test sample is placed on a white and black cardboard and two different measurements are carried out: one against the black background and the other against the white background: opacity is the ratio % between the evaluation against the black background and the white background. The higher is the %, the higher is opacity and the lower is transparency.

In table V the results of the application tests for the evaluation of exudation and transparency on flexible PVC are reported. The comparison is made among compositions 3 and 4, that are again reported below for better understanding, and a similar composition of flexible PVC containing the monomeric 1,3-dimethylamino uracyl (Composition 5).
Compositions 3, 4, 5 (numbers refer to parts in weight):

|  | Composition 3 | Composition 4 | Composition 5 |
|---|---|---|---|
| S-PVC (k value 70) | 100 | 100 | 100 |
| Dioctyl phthalate | 60 | 60 | 60 |
| Stearic acid | 0.2 | 0.2 | 0.2 |
| Epoxidized soy-bean oil* | 2 | 2 | 2 |
| Compound of Example 1 | — | 0.4 | — |
| 1,3-dimethyl-6-amino uracyl | — | — | 0.4 |

*oxyranic oxygen > 6 g (O$_2$)/100 g

TABLE V

Exudation and transparency

| Composition | Exudation value | Transparency % |
|---|---|---|
| 3 | 0 | 16.0 |
| 4 | 0 | 16.9 |
| 5 | 3 | 21.2 |

In Table V (a) the results of the application tests for the evaluation of exudation and transparency on some other flexible PVC compositions (Compositions 8, 9, 16, 19, 22, 23) are reported.

TABLE V

(a)-Exudation and Transparency

| Composition | Degree of Exudation | Transparency % |
|---|---|---|
| 8 | 0 | 16.6 |
| 9 | 0 | 16.3 |
| 16 | 0 | 16.7 |
| 19 | 0 | 18.4 |
| 22 | 0 | 15.7 |
| 23 | 3 | 24.6 |

We claim:

1. A flexible PVC composition exhibiting high thermal and oxidative stability comprising a flexible PVC and a stabililzer wherein the stabilizer is a compound selected from the group consisting of oligomieric aminouracyls, polymeric aminouracyls and mixtures thereof and having a structure of:

(a) repeating units of general formula (I):

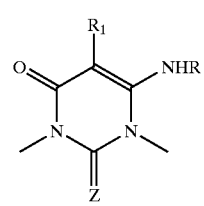

wherein:
R is selected from the group consisting of H; a $C_1$–$C_{18}$ linear or branched alkyl; a $C_5$–$C_8$ cycloalkyl; an aryl; an aryl substituted with —OH or $C_1$–$C_8$ alkoxy; an arylalkyl; an alkylaryl; and mixtures thereof;

$R_1$ is selected from the group consisting of H; a —(C=O)—$C_1$–$C_{12}$ linear or branched alkyl; a —(C=O)—O—$C_1$–$C_{12}$ linear or branched alkyl; a —(C=O) phenyl, wherein the phenyl is unsubstituted or substituted with —OH; a $C_1$–$C_8$ linear or branched alkyl; a $C_1$–$C_8$ alkoxy; and mixtures thereof; and Z is O or S;

(b) linking groups between the repetitive groups of formula (I) which are the same or different and are selected from the group consisting of: —(CR$_2$R$_3$)$_n$—, wherein n is an integer having a value of from 2 to 12 and R$_2$ and R$_3$ can be the same or different and each independently of the other is selected from the group consisting of H, a $C_1$–$C_{12}$ linear, branched or cyclic alkyl, and mixtures thereof; 3-methylene-3,5,5-trimethylcyclohexan-1-yl; methylenebis(4-cyclohexyl); methylenebis(3-cyclohexyl); 1,4-

|  | Comp. 8 | Comp. 9 | Comp. 16 | Comp. 19 | Comp. 22 | Comp. 23 |
|---|---|---|---|---|---|---|
| S-PVC k value 70 | 100 | 100 | 100 | 100 | 100 | 100 |
| Dioctyl phthalate | 60 | 60 | 60 | 60 | 60 | 60 |
| Stearic Acid | 0.5 | 0.5 | 0.5 | 0.5 | 0.5 | 0.5 |
| Epoxidized soy-bean oil* | 2 | 2 | 2 | 2 | 2 | 2 |
| Compound of Example 1 | 0 | 0 | 1 | 0 | 0 | 0 |
| Compound of Example 4 | 0.4 | 0 | 0 | 1 | 0 | 0 |
| Compound of Example 6 | 0 | 0.4 | 0 | 0 | 1 | 0 |
| 1,3-dimethyl-6-amino uracyl | 0 | 0 | 0 | 0 | 0 | 1 |

*oxyranic oxygen > 6 g (O$_2$)/100 g phenylene; 1-methyl-2,4-phenylene; and 4,4'-diphenylenemethane; and mixtures thereof;

(c) terminal groups selected from the group consisting of: H; a $C_1$–$C_{18}$ linear or branched alkyl; a $C_5$–$C_8$ cycloalkyl; a $C_3$–$C_{18}$ alkenyl; an aryl; an aryl substituted with —OH or $C_1$–$C_8$ alkoxy; an arylalkyl; an alkylaryl; a $C_1$–$C_{18}$ hydroxyalkyl; a $C_2$–$C_{18}$ alkoxy alkyl; a $C_6$–$C_{10}$ cycloalkoxyalkyl; a $C_7$–$C_{14}$ alkoxyaryl; a $C_7$–$C_{14}$ aryloxyalkyl; a $C_2$–$C_8$ alkylthioalkyl; a $C_6$–$C_{10}$ cycloalkylthioalkyl; a $C_7$–$C_{14}$ alkylthioaryl; a $C_7$–$C_{14}$ arylthioalkyl; a $C_1$–$C_{18}$ alkylamine, disubstituted with a $C_1$–$C_{18}$ linear or branched alkyl; and mixtures thereof.

2. A flexible PVC composition according to claim 1, wherein

R is selected from the group consisting of: H, a $C_1$–$C_{18}$ linear or branched alkyl, a $C_5$–$C_8$ cycloalkyl, an aryl, an aryl substituted with —OH or $C_1$–$C_8$ alkoxy; and mixtures thereof;

$R_1$ is H; and the terminal groups are selected from the group consisting of: H; a $C_1$–$C_{18}$ linear or branched alkyl; a $C_5$–$C_8$ cycloalkyl; a $C_3$–$C_{18}$ alkenyl; an aryl; an aryl substituted with —OH or $C_1$–$C_8$ alkoxy; a $C_1$–$C_{18}$ alkylamine, disubstituted with $C_1$–$C_{18}$ linear or branched alkyl; and mixtures thereof.

3. The flexible PVC composition according to claim 1, wherein the stabilizer is incorporated in an amount of from 0.01 to 10 percent by weight.

4. The flexible PVC composition according to claim 3, wherein the stabilizer is in an amount of from 0.05 to 5% by weight.

5. Flexible PVC compositions according to claim 4, wherein the stabilizer is incorporated in an amount from 0.1 to 3% by weight.

6. A stabilizer composition suitable for the stabilization of flexible PVC comprising an oligomeric and/or polymeric aminouracyl compound having a structure of: (a) repeating units of general formula (I):

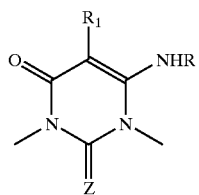

(I)

wherein:

R is selected from the group consisting of H; a $C_1$–$C_{18}$ linear or branched alkyl; a $C_5$–$C_8$ cycloalkyl; an aryl; an aryl substituted with —OH or $C_1$–$C_8$ alkoxy; an arylalkyl; an alkylaryl; and mixtures thereof;

$R_1$ is selected from the group consisting of H; a —(C=O)—$C_1$–$C_{12}$ linear or branched alkyl; a —(C=O)—O—$C_1$–$C_{12}$ linear or branched alkyl; a —(C=O) phenyl, wherein the phenyl is unsubstituted or substituted with —OH; a $C_1$–$C_8$ linear or branched alkyl; a $C_1$–$C_8$ alkoxy; and mixtures thereof; and Z is O or S;

(b) linking groups between the repetitive groups of formula (I) which are the same or different and are selected from the group consisting of: —$(CR_2R_3)_n$—, wherein n is an integer having a value of from 1 to 12 and $R_2$ and $R_3$ can be the same or different and each independently of the other is selected from the group consisting of H, a $C_1$–$C_{12}$ linear, branched or cyclic alkyl, and mixtures thereof; 3-methylene-3,5,5-trimethylcyclohexan-1-yl; methylenebis(4-cyclohexyl); methylenebis(3-cyclohexyl); 1,4-phenylene; 1-methyl-2,4-phenylene; and 4,4'-diphenylenemethane;

(c) terminal groups selected from the group consisting of: H; a $C_1$–$C_{18}$ linear or branched alkyl; a $C_5$–$C_8$ cycloalkyl; a $C_3$–$C_{18}$ alkenyl; an aryl; an aryl substituted with —OH or $C_1$–$C_8$ alkoxy; an arylalkyl; an alkylaryl; a $C_1$–$C_{18}$ hydroxyalkyl; a $C_2$–$C_{18}$ alkoxy alkyl; a $C_6$–$C_{10}$ cycloalkoxyalkyl; a $C_7$–$C_{14}$ alkoxyaryl; a $C_7$–$C_{14}$ aryloxyalkyl; a $C_2$–$C_8$ alkylthioalkyl; a $C_6$–$C_{10}$ cycloalkylthioalkyl; a $C_7$–$C_{14}$ alkylthioaryl; a $C_7$–$C_{14}$ arylthioalkyl; a $C_1$–$C_{18}$ alkylamine, disubstituted with a $C_1$–$C_{18}$ linear or branched alkyl; and mixtures thereof.

7. The compound according to claim 6, wherein

R is selected from the group consisting of: H, a $C_1$–$C_{18}$ linear or branched alkyl, a $C_5$–$C_8$ cycloalkyl, an aryl, an aryl substituted with —OH or $C_1$–$C_8$ alkoxy, and mixtures thereof;

$R_1$ is H;

and the terminal groups are selected from the group consisting of: H; a $C_1$–$C_{18}$ linear or branched alkyl; a $C_5$–$C_8$ cycloalkyl; a $C_3$–$C_{18}$ alkenyl; an aryl; an aryl substituted with —OH or $C_1$–$C_8$ alkoxy; a $C_1$–$C_{18}$ alkylamine, disubstituted with $C_1$–$C_{18}$ linear or branched alkyl; and mixtures thereof.

8. The compound according to claim 6, characterized by the fact that they can be obtained by cyclization using cyanacetic acid or its derivatives of an oligomeric and/or polymeric urea obtained by oligomerization and/or polymerization using combinations of:

(A) a diisocyanate (DD) of formula OCN—Y—NCO wherein Y is selected from the group consisting of: —$(CR_2R_3)_n$—, wherein n is an integer having a value of from 2 to 12 and $R_2$ and $R_3$ are the same or different and each independently of the other is selected from the group consisting of H, a $C_1$–$C_{12}$ linear or branched or cyclic alkyl, and mixtures thereof; 3-methylene-3,5,5-trimethylcyclohexan-1-yl; methylenebis(4-cyclohexyl); methylenebis(3-cyclohexyl); 1,4-phenylene; 1-methyl-2,4-phenylene; and 4,4'-diphenylenemethane; and mixtures thereof;

(B) an amine (A) of the general formula X—$NH_2$ wherein X is selected from the group consisting of: H; a $C_1$–$C_{18}$ linear or branched alkyl; a $C_5$–$C_8$ cycloalkyl; $C_3$–$C_{18}$ alkenyl; an aryl; an aryl substituted with —OH or $C_1$–$C_8$ alkoxy; an arylalkyl; an alkylaryl; a $C_1$–$C_{18}$ hydroxyalkyl; a $C_2$–$C_{18}$ alkoxy alkyl; a $C_6$–$C_{10}$ cycloalkoxyalkyl; a $C_7$–$C_{14}$ alkoxyaryl; a $C_7$–$C_{14}$ aryloxyalkyl; a $C_2$–$C_8$ alkylthioalkyl; a $C_6$–$C_{10}$ cycloalkylthioalkyl; a $C_7$–$C_{14}$ alkylthioaryl; a $C_7$–$C_{14}$ arylthioalkyl; $C_1$–$C_{18}$ alkylamine, disubstituted with $C_1$–$C_{18}$ linear or branched alkyl; and mixtures thereof;

(C) a diamine (AA) of the general formula $H_2N$—K—$NH_2$ wherein K is selected from the group consisting of:—$(CR_2R_3)_n$—, wherein n is an integer having a value of 2 to 12 and $R_2$, $R_3$ are the same or different and each independently of the other is selected from the group consisting of H, a $C_1$–$C_{12}$ linear or branched or cyclic alkyl when n is equal to or greater than 2; and mixtures thereof; 3-methylene-3,5,5-trimethylcyclohexan-1-yl; methylenebis(4-cyclohexyl); methylenebis(3-cyclohexyl); 1,4- phenylene; 1-methyl-2,4-phenylene; and 4,4'-diphenylenemethane; and mixtures thereof; and (D) an isocyanate of formula W—NCO (D), where W is selected from the group consisting of: a $C_1$–$C_{18}$ linear or branched alkyl; a $C_5$–$C_8$ cycloalkyl; a $C_3$–$C_{18}$ alkenyl; an aryl; an aryl substituted with —OH or $C_1$–$C_8$ alkoxy; an arylalkyl; an alkylaryl; a $C_1$–$C_{18}$ hydroxyalkyl; a $C_2$–$C_8$ alkoxy alkyl; a $C_6$–$C_{10}$ cycloalkoxyoalkyl; a $C_7$–$C_{14}$ alkoxyaryl; a $C_7$–$C_{14}$ aryloxyalkyl; $C_1$–$C_{18}$ alkylamine, disubstituted with $C_1$–$C_{18}$ linear or branched alkyl; and mixtures thereof.

9. The compound according to claim 8, wherein in the preparation of the polyurea, when AA and D are both equal to zero, the molar ratio of DD/A is from 0.3 to 0.6; and when DD and A are both equal to zero, the molar ratio of AA/D is from 0.3 to 0.6.

* * * * *